(12) United States Patent
Reign

(10) Patent No.: US 12,303,710 B2
(45) Date of Patent: May 20, 2025

(54) PENIS PHOTOTHERAPY DEVICE

(71) Applicant: Dynamic Medical Technologies Inc., Clearwater, FL (US)

(72) Inventor: Vivienne Reign, Irvine, CA (US)

(*) Notice: Subject to any disclaimer, the term of this patent is extended or adjusted under 35 U.S.C. 154(b) by 582 days.

(21) Appl. No.: 17/649,709

(22) Filed: Feb. 2, 2022

(65) Prior Publication Data

US 2022/0152416 A1 May 19, 2022

Related U.S. Application Data

(63) Continuation-in-part of application No. 16/834,770, filed on Mar. 30, 2020, now abandoned.

(51) Int. Cl.
*A61N 5/06* (2006.01)

(52) U.S. Cl.
CPC .... *A61N 5/0613* (2013.01); *A61N 2005/0626* (2013.01); *A61N 2005/0645* (2013.01); *A61N 2005/0652* (2013.01); *A61N 2005/0659* (2013.01); *A61N 2005/0663* (2013.01)

(58) Field of Classification Search
CPC ...... A61N 5/06–2005/073; A61B 2018/20351; A61B 2018/2065; A61B 2018/2211; A61B 18/20–18/28
USPC ..................... 607/88–94; 606/2–19
See application file for complete search history.

(56) References Cited

U.S. PATENT DOCUMENTS

| 6,241,752 B1 | 6/2001 | Sheinman | |
| 2008/0312709 A1* | 12/2008 | Volpe | A61B 5/339 607/6 |
| 2014/0303693 A1* | 10/2014 | Haarlander | A61N 5/0616 607/91 |
| 2015/0238774 A1* | 8/2015 | Anderson | A61L 26/0066 604/20 |

FOREIGN PATENT DOCUMENTS

| CN | 111110997 A | * | 5/2020 | ....... A61F 13/00063 |
| KR | 20060127450 A | * | 6/2005 | ............... A61N 5/06 |

* cited by examiner

*Primary Examiner* — Jonathan T Kuo
*Assistant Examiner* — Vynn V Huh
(74) *Attorney, Agent, or Firm* — Distinct Patent Law; Justin P. Miller

(57) ABSTRACT

The penis phototherapy device can surround a body part, such as a penis, to provide light therapy to all sides. The primary elements of the penis phototherapy device include: a flexible base material; a light emitting array affixed to a flexible circuit board; a clear and flexible array cover material; a controller with electronics and a power source; elements to removably affix the flexible base material to itself to cause the device to surround a body part, and slots that allow a user to wear the penis phototherapy device attached to a belt. When used to treat a penis, the light improves sexual ability and health and reduces symptoms of erectile dysfunction.

10 Claims, 9 Drawing Sheets

PENIS PHOTOTHERAPY DEVICE

CROSS-REFERENCE TO RELATED APPLICATION

This application is a continuation-in-part of U.S. patent application Ser. No. 16/834,770, filed Mar. 30, 2020, titled PHOTOTHERAPEUTIC DEVICE FOR A PENIS AND A USING METHOD THEREOF.

FIELD

This invention relates to the field of phototherapy and more particularly to a device for phototherapy of the penis.

BACKGROUND

Light is an effective treatment for multiple disorders. It can increase blood flow, treat skin conditions, and improve overall health.

Effectiveness of light as a treatment is hampered by the difficulty in applying it to a specific area for a long period of time. Patients may not be willing or able to spend sufficient time with a device applied to an area to receive full therapeutic benefit.

Additionally, certain areas of the body are difficult to fully treat with light due to shape or location.

What is needed is a device that conforms to the shape of parts of the body while being portable to allow the user to benefit from long-term application.

SUMMARY

The penis phototherapy device can surround a body part, such as a penis, to provide light therapy to all sides.

The primary elements of the penis phototherapy device include: a flexible base material; a light emitting array affixed to a flexible circuit board; a clear and flexible array cover material; a controller with electronics and a power source; elements to removably affix the flexible base material to itself to cause the device to surround a body part, and slots that allow a user to wear the penis phototherapy device attached to a belt.

When used to treat a penis, the light improves sexual ability and health and reduces symptoms of erectile dysfunction.

These two sections of the device are separated into an enclosing section and an attaching section. The enclosing section is intended to surround the penis. The attachment section is intended to be connected to the user by, for example, a belt.

The enclosing section and the attachment section are separated by a notch that creates a gap. This gap allows the user's testicles to stay outside of the area of light treatment, thus avoiding exposure of the testicles to the light. This minimizes heating the testicles, which can cause fertility problems.

The enclosing section includes two positions: a flat position and a rolled/bent position. The enclosing section preferably has a square or rectangular shape.

In the flat position, which is the natural position of the device, the enclosing section is preferably rectangular.

In the rolled position the two outer edges are overlapped, in the preferred embodiment forming a cylinder. The overlapping edges include attachment mechanisms. In the preferred embodiment the attachment mechanisms are magnets. The attachment mechanism can be a single magnet that interfaces with a metal strip, for example steel strip. Alternatively, the attachment mechanism can be two magnetic strips that would are arranged to have opposing polarities.

The attachment section preferably includes two slots to allow it to be affixed over a user's belt. This allows the device to be worn during the day, under one's clothing.

Turning to the therapeutic elements of the device, the elements that provide light therapy are primarily connected by the flexible circuit board. The array of light emitting elements, for example LEDs, is affixed the flexible circuit board. The flexible circuit board connects the light emitting elements to the controller, carrying both signal information and power information.

The use of a flexible circuit board allows the device to be bent around a body part, while maintaining connectivity of the light emitting elements. The use of a flexible circuit board further avoids hard edges that would be caused by a collection of individual rigid circuit boards.

The flexible circuit board also allows the device to return to a flat position for storage and shipping. The flat position is the natural shape of the device, and thus the shape to which it will return unless otherwise attached.

The light emitting elements are spread across the circuit board to create a near-continuous light field. The quantity and spacing of LEDs can be adjusted depending upon the power requirements of the LEDs and their light output. For example, if the device is constructed of LEDs that have a high power output, the spacing can be increased to avoid overexposure. But, if the device is constructed of LEDs that have a lower power output, the LEDs can be placed more closely together.

The use of discrete lighting elements allows for intermixing of different emission wavelengths. For example, the wavelengths of light delivered by the light emitting array can range from about 600 nm to about 900 nm. This includes the specific ranges of red light (wavelength 625 nm-680 nm) and infrared light (wavelength 810 nm-910 nm).

The LED array is shielded by a flexible transparent material. For example, TPE (thermoplastic elastomer), TPU (thermal plastic polyurethane), or similar. The flexible transparent material protects the underlying light emitting devices from liquids and debris and allows for easy cleaning of the device.

The controller includes an internal replaceable battery. The battery is sized such that multiple treatments can be performed on a single charge, and the device can be operated unplugged. Thus, the user is unencumbered during the course of treatment.

The controller includes an internal timer to avoid overtreatment. The standard treatment time is 20 minutes.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
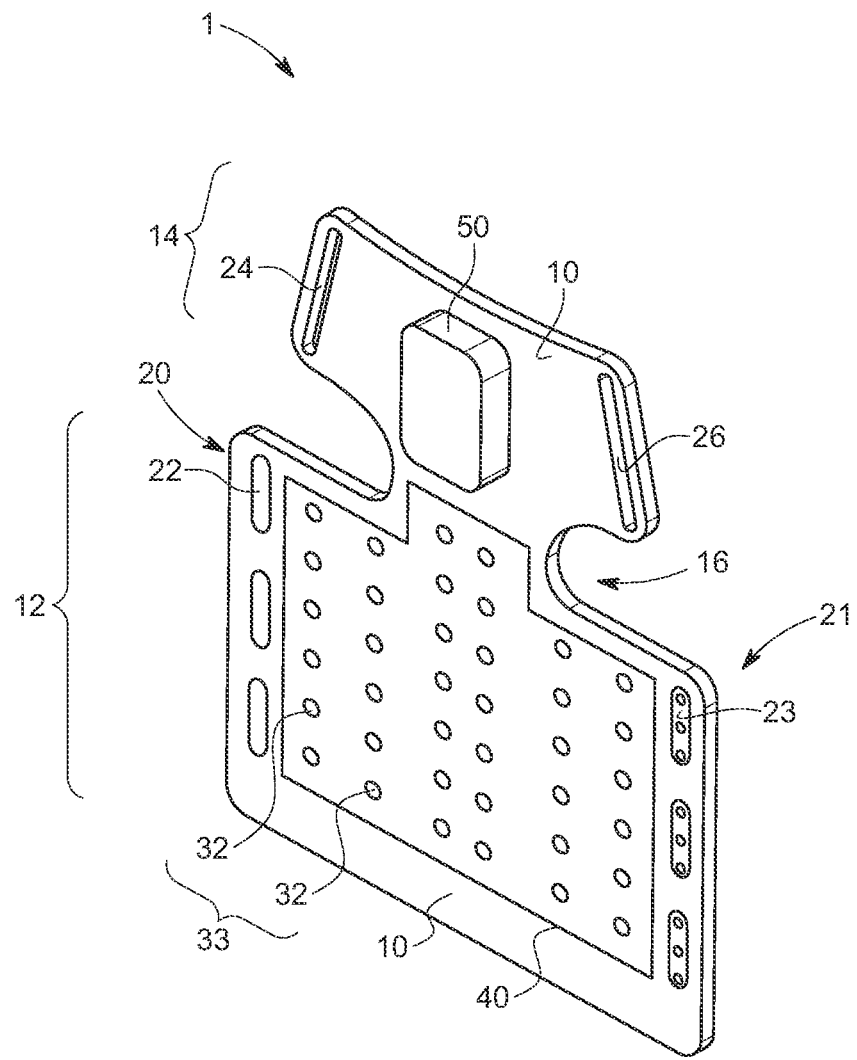
FIG. 1 illustrates a first isometric view of the penis phototherapy device.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a first isometric view of the penis phototherapy device is shown.

The phototherapy device 1 is shown formed from body 10, body 10 including an enclosing section 12 and an attaching section 14 separated by notch 16.

The attaching section 14 includes a first attachment slot 24 and a second attachment slot 26 for a user's belt. In combination with the belt, the first attachment slot 24 and the second attachment slot 26 hold the phototherapy device 1 against the user's body.

The enclosing section 12 has two edges that affix to each other to form a rolled shape. The rolled shape is created by attaching the first attachment element 20 to the second attachment element 21.

The first attachment element 20 is shown with magnets 22, and the second attachment element 21 with metal plates 23. Other means of affixing the first attachment element 20 to the second attachment element 21 are anticipated, including hook and loop tape or latches.

Also shown are multiple light-emitting elements 32, creating a light-emitting array 33, beneath the encapsulating membrane 40.

The controller 50 provides both power and signal data to the multiple light-emitting elements 32.

Figure 2:
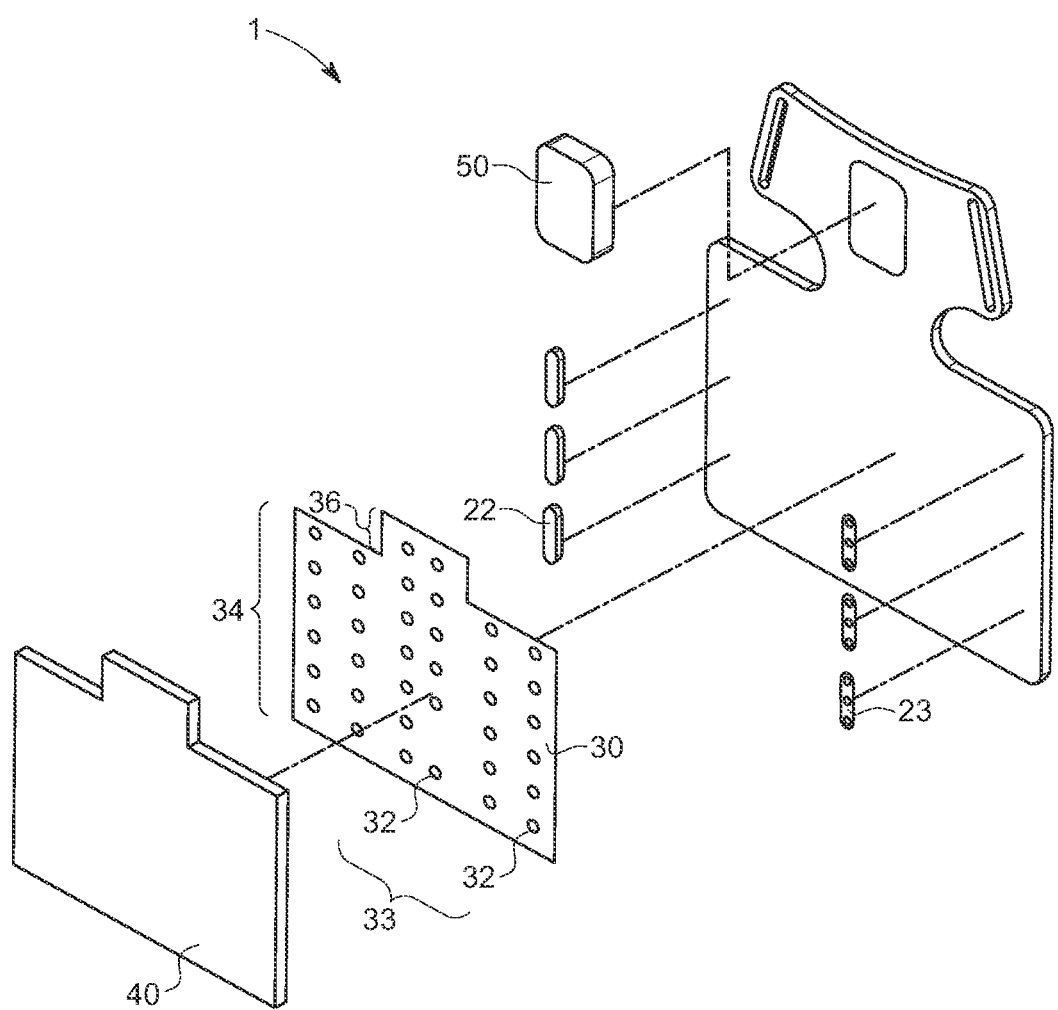
FIG. 2 illustrates a first exploded view of the penis phototherapy device.

Referring to FIG. 2, a first exploded view of the penis phototherapy device is shown.

The flexible circuit board 30 is shown with a plurality of light-emitting elements 32.

The flexible circuit board 30 is optionally divided into a primary module 34 and a secondary module 36.

The primary module 34 will completely surround the penis. The secondary module 36 is an extension that will cover the top of the penis while allowing space underneath for the testicles to exit the phototherapy device 1.

The magnets 22 and metal plates 23 are shown as discrete, disconnected elements. In alternative embodiments the magnet 22 is a single linear piece, and the metal plate 23 is a single linear piece.

The encapsulating membrane 40 covers and protects the flexible circuit board 30 and light-emitting elements 32.

Figure 3:
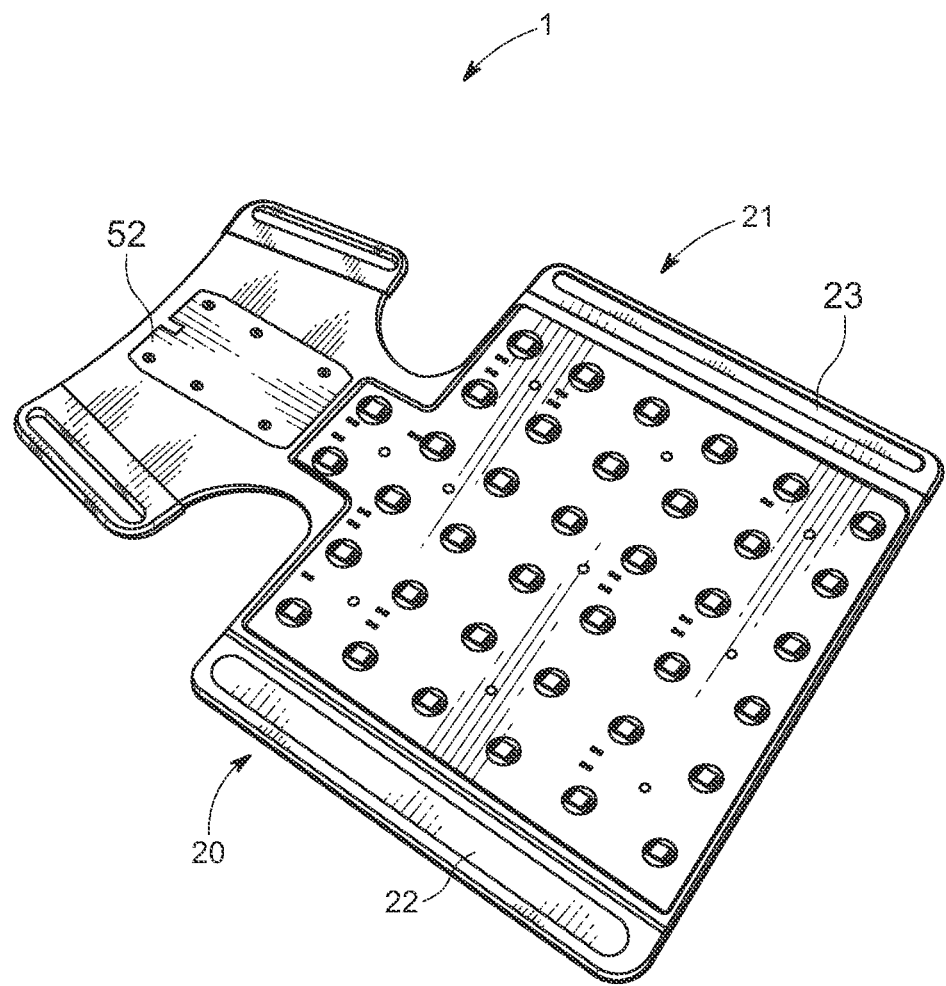
FIG. 3 illustrates a second isometric view of the penis phototherapy device.

Referring to FIG. 3, a second isometric view of the penis phototherapy device is shown.

The phototherapy device 1 is shown with first attachment element 20 with magnets 22, and second attachment element 21 with metal plates 23.

Also shown is controller cover 52.

Figure 4:
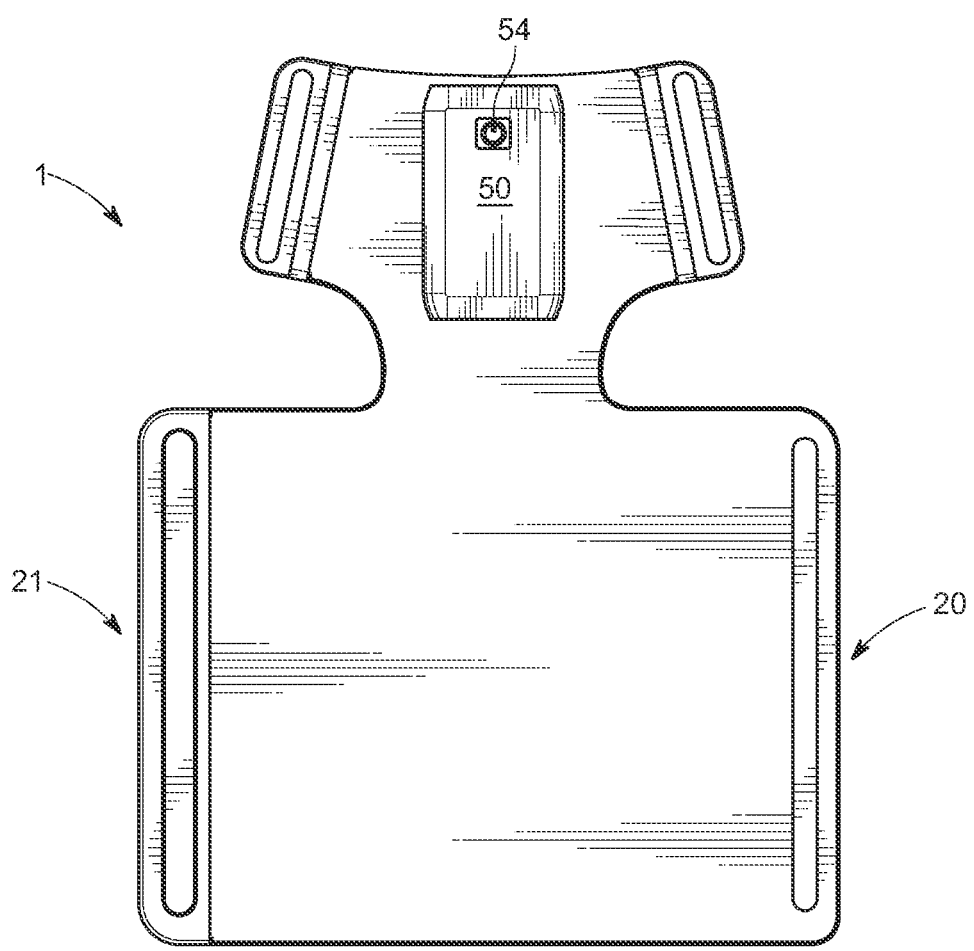
FIG. 4 illustrates a back view of the penis phototherapy device.
Figure 5:
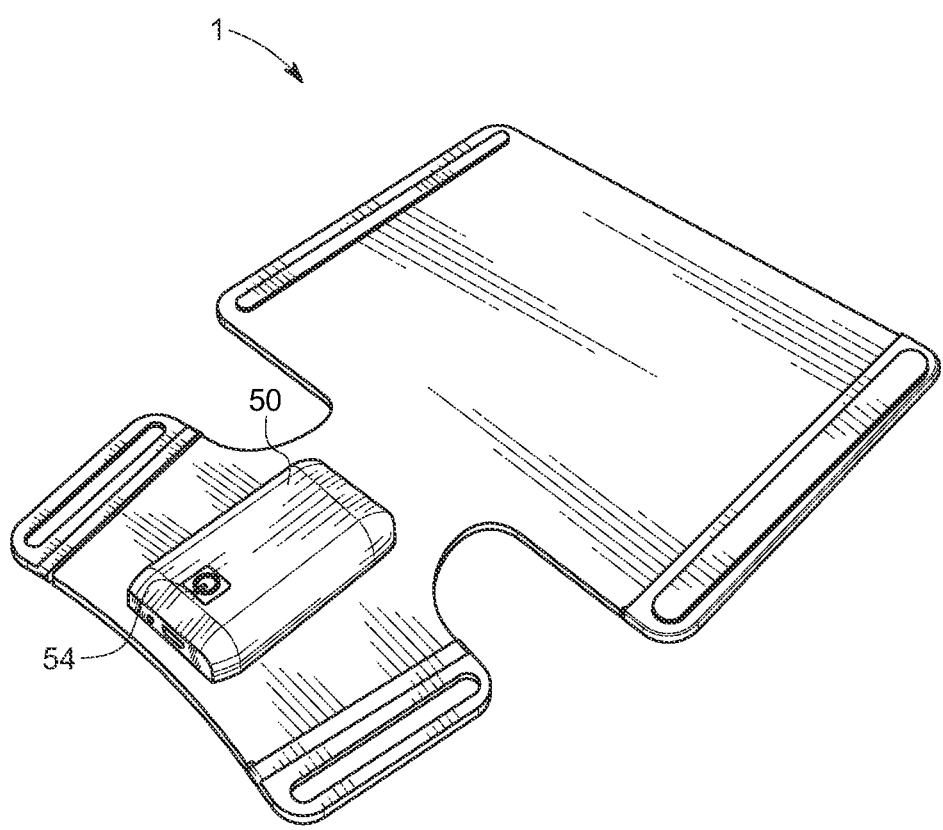
FIG. 5 illustrates a back isometric view of the penis phototherapy device.

Referring to FIGS. 4 and 5, a back view and back isometric view of the penis phototherapy device are shown.

The phototherapy device 1 is shown with first attachment element 20, second attachment element 21, controller 50 and controller power button 54.

Figure 6:
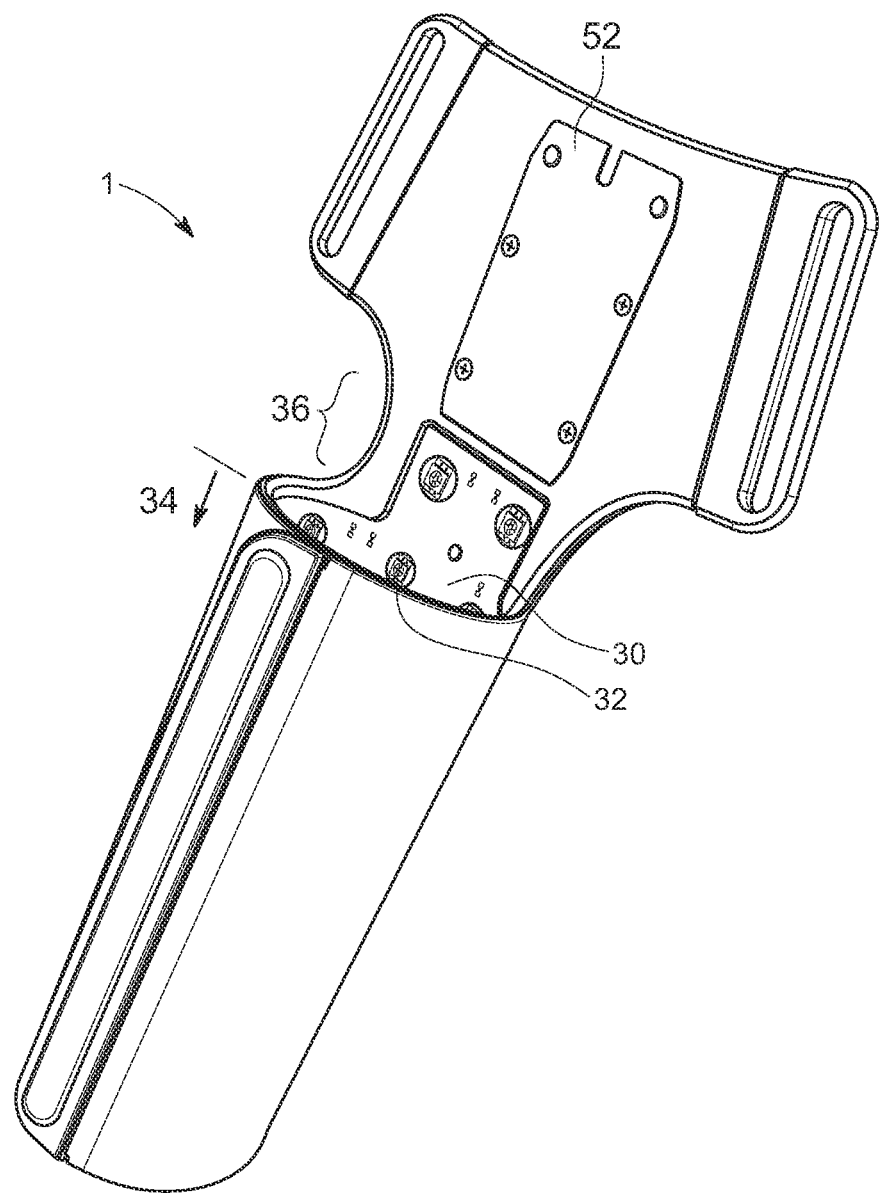
FIG. 6 illustrates a first rolled view of the penis phototherapy device.

Referring to FIG. 6, a first rolled view of the penis phototherapy device is shown.

Then the phototherapy device 1 is in the rolled position, the flexible circuit board 30 with multiple light-emitting elements 32 is shaped to surround the penis. The flexible circuit board 30 is shown divided into its primary module 34 and secondary module 36.

Figure 7:
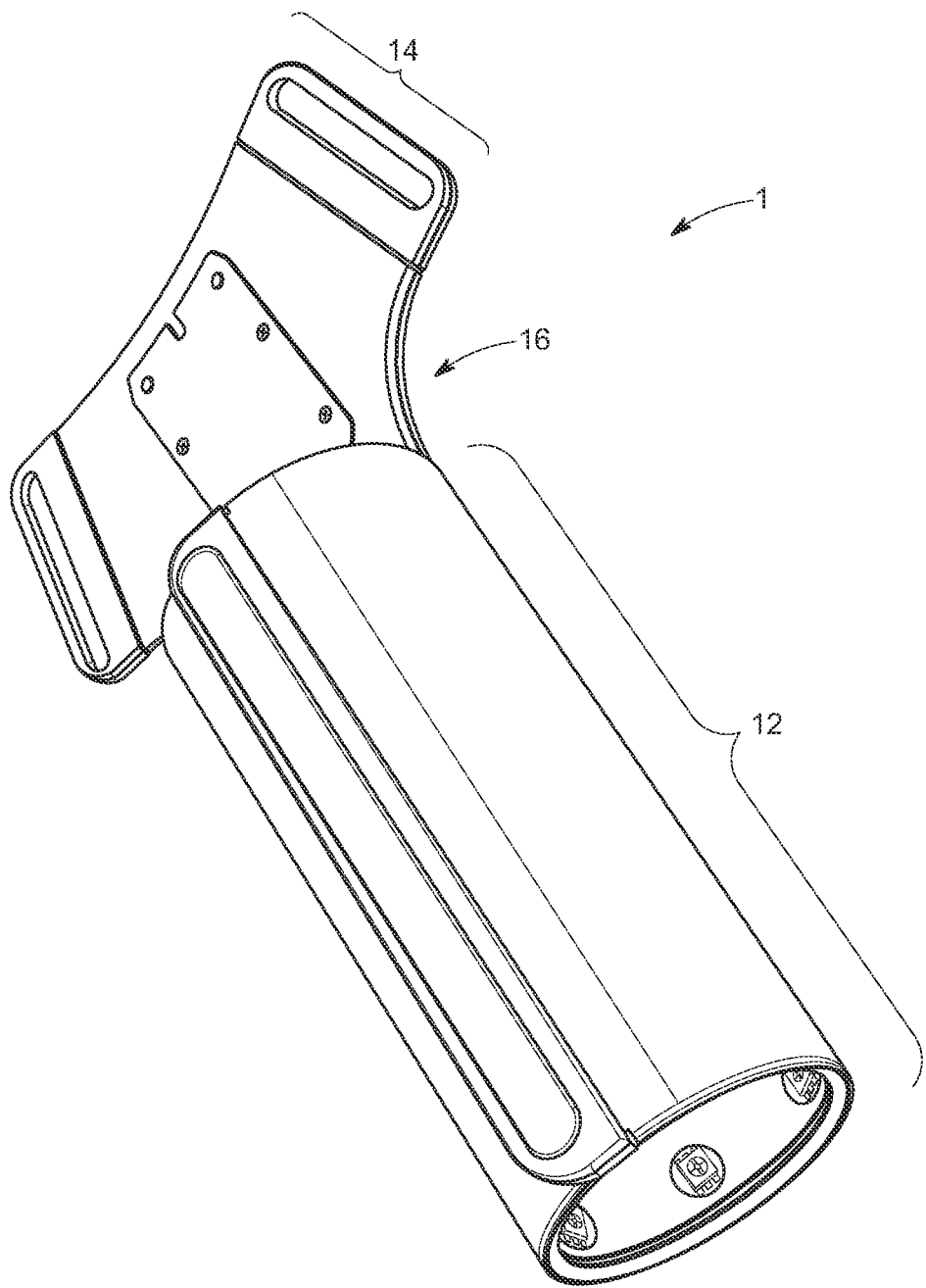
FIG. 7 illustrates a second rolled view of the penis phototherapy device.
Figure 8:
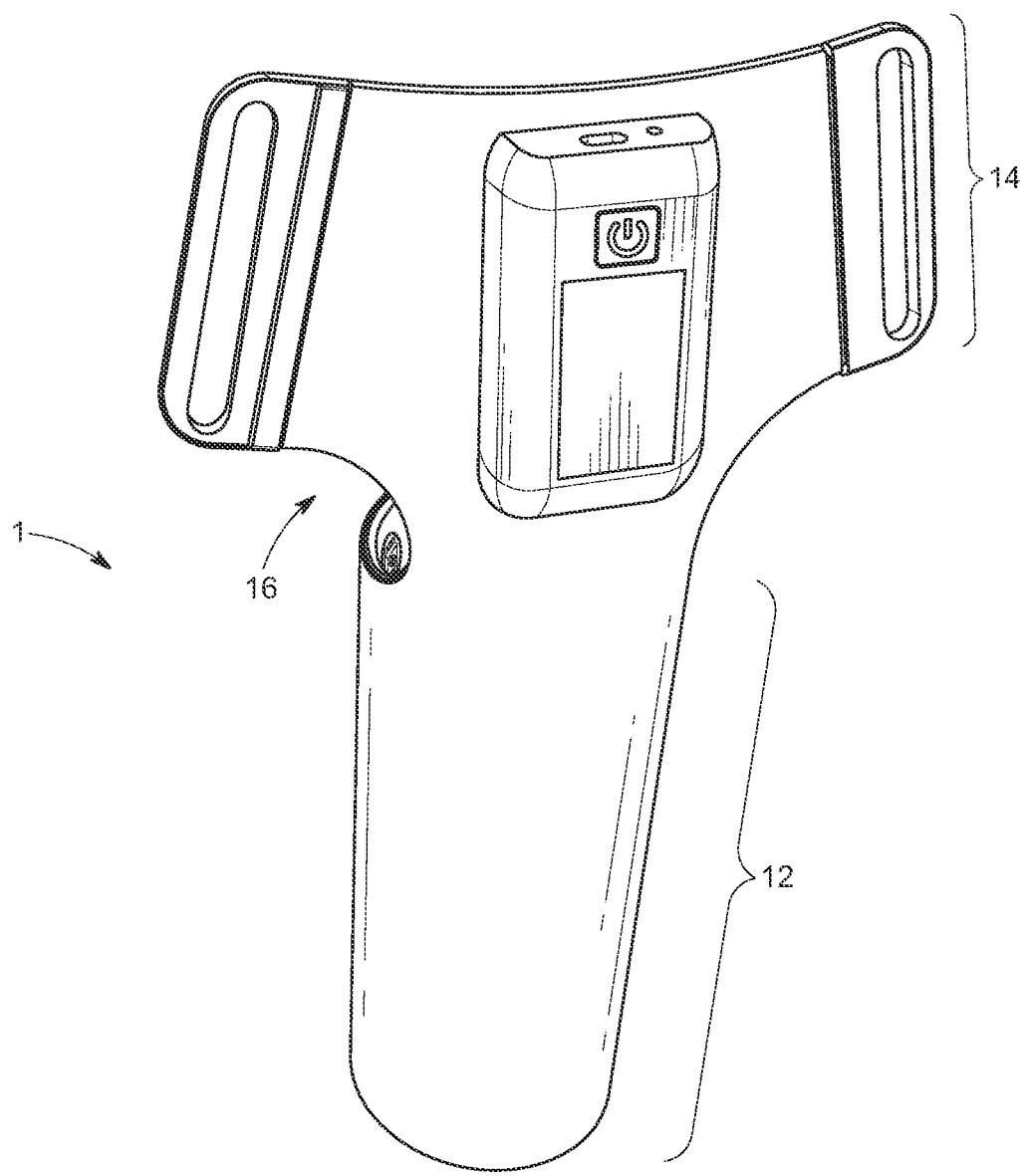
FIG. 8 illustrates a third rolled view of the penis phototherapy device.
Figure 9:
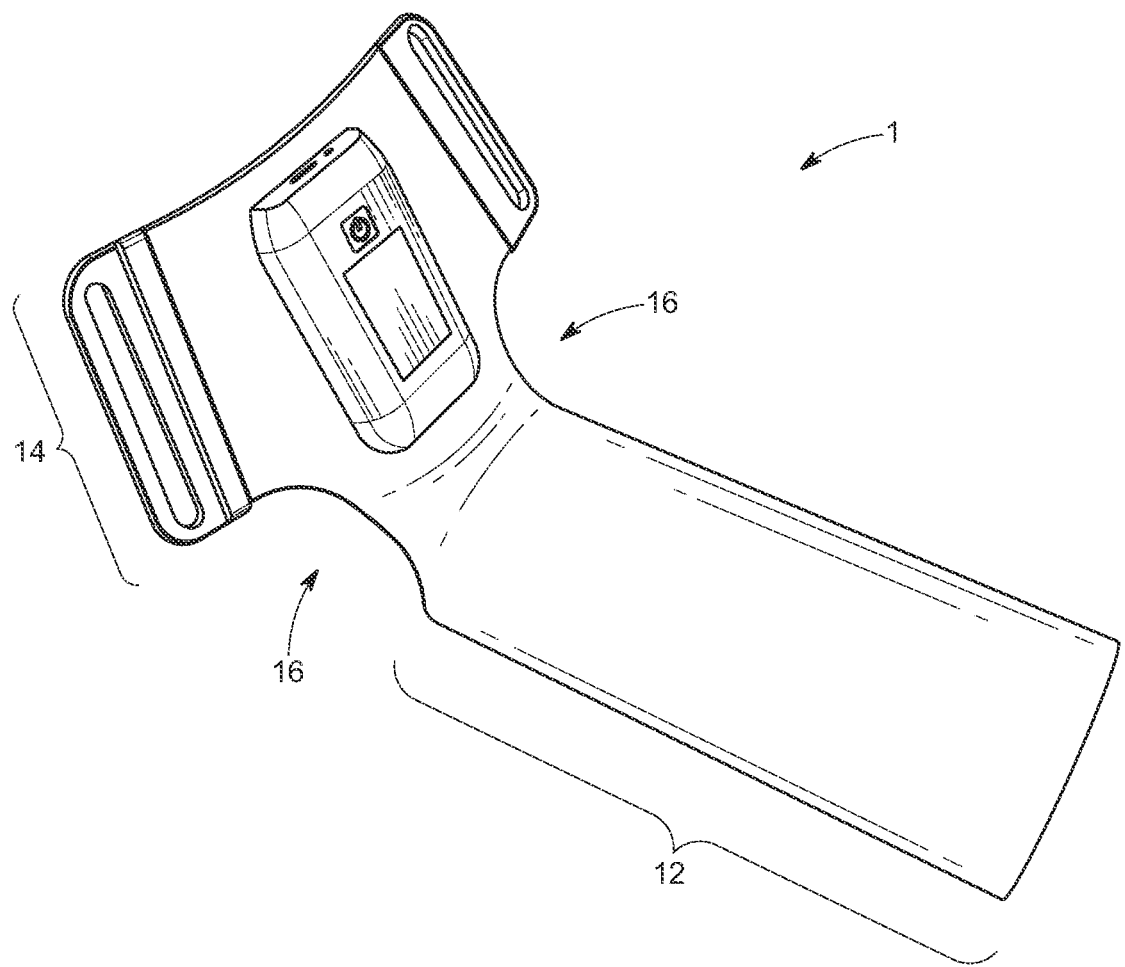
FIG. 9 illustrates a fourth rolled view of the penis phototherapy device.

Referring to FIGS. 7, 8, and 9, multiple views of the penis phototherapy device in a rolled, or enclosing, orientation are shown.

The phototherapy device 1 includes enclosing section 12 and attaching section 14 divided by notch 16. The notch 16 creates a gap that allows the testicles to exit the device, avoiding exposing the testicles to the light therapy.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device to treat a penis of a user using light therapy, while avoiding treatment of testicles, the device comprising:
   an enclosing section;
      the enclosing section including a first attachment element and a second attachment element;
      the enclosing section having a first position and a second position;
         the first position being flat;
            the first attachment element unaffixed from the second attachment element, allowing the enclosing section to unroll to the first position;
         the second position being rolled;
            the first attachment element affixed to the second attachment element to hold the enclosing section in the second position;
         the enclosing section opening to the flat first position whenever the first attachment element is unfixed from the second attachment element;
   a flexible circuit board with a plurality of light-emitting elements;
      the plurality of light-emitting elements protected by an encapsulating membrane;
      the plurality of light-emitting elements emitting light toward the penis when the enclosing section is in the second position; and
      the plurality of light-emitting elements are spaced apart based on their respective power outputs to create a near-continuous light field;
   an attaching section;
      the attaching section fixing to a belt of the user;
      the attaching section including two or more slots to affix to the belt while allowing the testicles to exit the device;
   the flexible circuit board further includes a primary module and a secondary module;
      the primary module is located within the enclosing section;

the secondary module is located between the enclosing section and the attaching section;
the primary module includes a first set of light-emitting elements of the plurality of light-emitting elements;
the secondary module includes a second set of light-emitting elements of the plurality of light-emitting elements; and
the secondary module including the second set of light-emitting elements treats a top of the penis above the testicles, but without shining light on the testicles; and
a first notch and a second notch;
the first notch is positioned on a first side of the secondary module and the second notch is positioned on a second side of the secondary module;
the first notch and the second notch each create a gap between the enclosing section and the attaching section that allows testicles to exit the device and avoid exposure to the light;
whereby the device uses light to therapeutically treat the user's penis.

2. The device to treat the penis of the user using light therapy of claim 1 further comprising: a controller; the controller affixed to the attaching section; whereby the controller powers and controls the plurality of light-emitting elements, making the device portable.

3. The device to treat the penis of the user using light therapy of claim 1 wherein: the first attachment element is one or more magnets; the second attachment element is one or more metal elements; the one or more magnets affixed to the one or more metal elements when the enclosing section is in the second position; whereby the user can attach and detach the first attachment element from the second attachment element to move the enclosing section between the first position and the second position.

4. The device to treat the penis of the user using light therapy of claim 3 further comprising: a controller; the controller affixed to the attaching section; whereby the controller powers and controls the plurality of light-emitting elements, making the device portable.

5. The device to treat the penis of the user using light therapy of claim 1 wherein: the plurality of light-emitting elements emit light at wavelengths of 625 nm-680 nm and 810 nm-910 nm.

6. A device for emitting light against a penis of a user to improve blood flow and sexual function, while not treating testicles, the device comprising:
an enclosing section inside of which the penis is treated;
the enclosing section including a flexible circuit board to which are attached a plurality of light-emitting elements;
the plurality of light-emitting elements shielded under an encapsulating membrane;
the plurality of light-emitting elements is spaced apart based on their respective power outputs to create a near-continuous light field;
the enclosing section having a naturally flat position, and a rolled position;
the enclosing section held in the rolled position by joining a first attachment element to a second attachment element;
an attaching section allowing the user to support the device in place with respect to the penis;
the flexible circuit board further includes a primary module and a secondary module;
the primary module is located within the enclosing section;
the secondary module is located between the enclosing section and the attaching section;
the primary module includes a first set of light-emitting elements of the plurality of light-emitting elements;
the secondary module includes a second set of light-emitting elements of the plurality of light-emitting elements; and
the secondary module including the second set of light-emitting elements treats a top of the penis above the testicles, but without shining light on the testicles;
the enclosing section and the attaching section separated by a notch in the secondary module; and
the testicles of the user hanging through a gap created by the notch, placing the testicles outside the enclosing section, thus preventing application of light to the testicles;
whereby the device applies light treatment to the penis without applying light to the testicles.

7. The device of claim 6 further comprising:
a controller;
the controller affixed to the attaching section;
whereby the controller powers and controls the plurality of light-emitting elements, making the device portable.

8. The device of claim 6 wherein:
the first attachment element is one or more magnets;
the second attachment element is one or more metal elements; and
the one or more magnets affixed to the one or more metal elements when the enclosing section is in the rolled position;
whereby the user can attach and detach the first attachment element from the second attachment element to move the enclosing section between the naturally flat position and the rolled position.

9. The device of claim 8 further comprising:
a controller;
the controller affixed to the attaching section;
whereby the controller powers and controls the plurality of light-emitting elements, making the device portable.

10. The device of claim 6 wherein:
the plurality of light-emitting elements emit light at wavelengths of 625 nm-680 nm and 810 nm-910 nm.

* * * * *